United States Patent [19]

Karwoski

[11] Patent Number: 5,037,296

[45] Date of Patent: Aug. 6, 1991

[54] LIP PROTECTOR FROM ORTHODONTIC WIRES AND BRACKETS

[76] Inventor: Thaddeus M. Karwoski, 5420-B Roundtree Ct., Concord, Calif. 94521

[21] Appl. No.: 573,473

[22] Filed: Aug. 27, 1990

[51] Int. Cl.⁵ .................................................. A61C 3/00
[52] U.S. Cl. .......................................... 433/8; 433/22
[58] Field of Search ................. 433/2, 8, 9, 10, 11, 433/12, 13, 14, 15, 16, 22

[56] References Cited

U.S. PATENT DOCUMENTS 4,512,740  4/1985  Kurz ........................................ 433/22
4,527,975  7/1985  Ghafari et al. .......................... 433/8
4,559,013  12/1985  Amstutz et al. ........................ 433/8
4,913,654  4/1990  Morgan et al. ......................... 433/8

Primary Examiner—John J. Wilson
Attorney, Agent, or Firm—Linval B. Castle

[57] ABSTRACT

An elongated strip of pliable resilient plastic for covering a patient's orthodontic brackets and wire reduces chafing and injury to the interior of the patient's mouth from sharp edges. The cover strip is attached to the wires between the orthodontic brackets by thin plastic wire locks on the rear surface of the strip and having horizontal wire engaging slits.

4 Claims, 1 Drawing Sheet

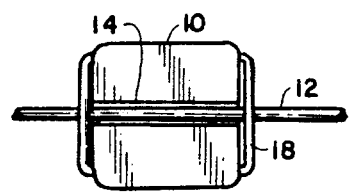
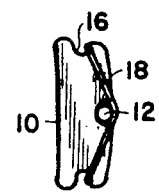
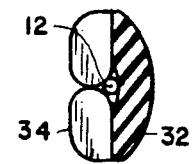
FIG. 1            FIG. 2            FIG. 4
FIG. 3
FIG. 5
FIG. 6

LIP PROTECTOR FROM ORTHODONTIC WIRES AND BRACKETS

BRIEF SUMMARY OF THE INVENTION

This invention relates to dental apparatus and in particularly to a smooth exterior band that connects to orthodontic wires to cover those wires and orthodontic brackets to thereby protect the delicate mouth interior and lips against sharp edges.

For both cosmetic or medical purposes, a large percentage of today's youth are requiring orthodontic treatment including the fastening of orthodontic wires to the exterior surface of the teeth to force them into a desired form. The orthodontic wires are fastened by elastic bands or sharp, thin, malleable wires to orthodontic brackets, small metal plates that are cemented to the faces of the teeth, and the wires are tightened as necessary and secured at their ends to a terminal cap usually located near the rear molars.

Orthodontic wires and brackets are thin and extend a minimal distance outward from the tooth face. Nevertheless, the installed wires present a rough surface that can irritate the tender inner flesh of the cheeks and lips and often a sharp wire or bracket edge can cause bleeding in the mouth.

Sharp ends on the orthodontic wires that easily cut into the inner cheek flesh are eliminated with the wire terminal described in my U.S. Pat. No. 4,797,094. Sharp or irritating edges on orthodontic brackets or their attached wires may be eliminated with the lip protector to be described herein.

Briefly described, the invention is for a lip protector comprising a thin pliable plastic or rubber strip having a width slightly greater than that of an orthodontic bracket and any suitable length, such as a length corresponding to the full row of teeth between right and left molars. The front surface of the strip is smooth and preferably of a color that is generally non-conspicuous against a row of teeth. The rear surface of the strip is flat except for a plurality of orthodontic wire "locks" spaced to generally correspond to the pitch of a teeth, i.e. teeth per inch. The lip protector strip may then be removably attached to cover the wires and brackets in a patient's jaw by merely snapping the wire locks to the orthodontic wire.

BRIEF DESCRIPTION OF THE DRAWINGS

In the drawings which illustrate the preferred embodiment of the invention:

FIG. 1 is a front elevation view of an orthodontic bracket with attached orthodontic wire;

FIG. 2 is a side elevational view of the bracket of FIG. 1;

FIG. 3 is a plan view of a lip protector attached to an orthodontic wire secured to an orthodontic bracket;

FIG. 4 is a sectional side view of the lip protector;

FIG. 5 is a rear elevational view of a lip protector; and

FIG. 6 is a front elevational view of the lip protector.

DETAILED DESCRIPTION

Illustrated in FIG. 1 is a typical orthodontic bracket 10 which is normally cemented to the face of a tooth and against which an orthodontic wire 12 bears. The bracket 10 is quite small and normally is about 0.15 to 0.20 inches in height and width with a shallow horizontal groove 14 for seating the wire 12. As shown in the side view of FIG. 2, the bracket contains top and bottom grooves 16 and a small elastic band or malleable wire 18 in both top and bottom grooves is looped over the orthodontic wire 12 to snugly hold the wire and bracket together.

FIG. 3 is a greatly enlarged top plan view of the orthodontic wire 12 attached by elastic bands or malleable wires to two orthodontic brackets 10, 20, which may be considered to be cemented to the faces of two adjacent teeth. FIG. 3 also illustrates the facing strip 32 of the lip protector which includes, in addition to the facing strip, a plurality of spaced wire locks 34 formed on the rear surface of the strip. The soft, pliable, lip protector is a separate and removable thin front cover for the wire 12 and brackets 10 and is attached to the orthodontic wires 12 by merely snapping the wire locks 34 over the wires 12 as shown in FIG. 4. In practice, both the facing strip 32 and wire lock 34 are about 0.05 inches in thickness; therefore, when installed, the soft surface of the lip protector will extend only about 0.05 inches beyond the orthodontic wire.

FIG. 4 is a side view of the lip protector showing the facing strip 32 in section. Each of the several wire locks 34 either attached to, or formed on the rear surface of the facing strip contain a central horizontal slit into which the orthodontic wire 12 may fit. If desired, the wire locks 34 may be in the form of a pair of closely fitting pillows, as shown, so that a wire 12 may be pressed between the pillows and into an open area between the pillows and the rear surface of the facing strip. In this form, the wire lock will secure the wire 12 within the open area and will resist its removal through the adjacent pillows of the wire lock.

FIG. 5 is a rear elevational view of the lip protector showing the plurality of wire locks 34 on the rear surface of the facing strip 32. The spacing of the wire locks on the strip should correspond to the spacing of a patient's teeth so that the locks 34 will be attached to the orthodontic wire between the locations of the orthodontic brackets. If a wire lock 34 happens to coincide with the position of a orthodontic bracket 32, the wire lock may easily be clipped from the rear of the facing strip 32. Thus, only one size lip protector may be used for all size jaws. FIG. 6 is a front elevational view of the lip protector showing the smooth exterior surface of the facing strip.

I claim:

1. A lip protector to be removably connected to an orthodontic wire to protect the interior of a patient's cheeks and lips from the edges of orthodontic brackets and wires, said lip protector comprising:

a thin elongated, resilient facing strip having a first surface and a smooth second surface, said facing strip having a width at least equal to the width of an orthodontic bracket; and a plurality of resilient wire locks on the first surface of said facing strip and spaced an amount corresponding to the normal spacing of a patients teeth, each wire lock in said plurality formed by a pair of adjacent pillow-like protrusions separated by a horizontal slit for engaging an orthodontic wire.

2. The lip protector claimed in claim 1 wherein each of said plurality of wire locks is resilient and narrower than the normal width of a patient's tooth, and wherein said horizontal slit extends through said wire lock to said first surface of said facing strip for engaging an orthodontic wire.

3. The lip protector claimed in claim 2 wherein the juncture of said two pillow-like protrusions and said first surface of said facing strip forming an open area for securing an orthodontic wire.

4. The lip protector claimed in claim 1 wherein said plurality of wire locks and said facing strip are formed into a single unit of pliable, resilient, material.

* * * * *